United States Patent [19]
Blagg et al.

[11] Patent Number: 5,912,357
[45] Date of Patent: Jun. 15, 1999

[54] INDOLE DERIVATIVES AS 5-α-REDUCTASE-1-INHIBITORS

[75] Inventors: Julian Blagg; Graham Nigel Maw, both of Sandwich; David James Rawson, Sandich, all of United Kingdom

[73] Assignee: Pfizer Inc, New York, N.Y.

[21] Appl. No.: 08/592,315

[22] PCT Filed: Aug. 2, 1994

[86] PCT No.: PCT/EP94/02563

§ 371 Date: Feb. 15, 1996

§ 102(e) Date: Feb. 15, 1996

[87] PCT Pub. No.: WO95/05375

PCT Pub. Date: Feb. 23, 1995

[30] Foreign Application Priority Data

Aug. 17, 1993 [GB] United Kingdom .................. 9317096

[51] Int. Cl.⁶ ................ C07D 405/06; C07D 405/14
[52] U.S. Cl. ............................................. 548/454
[58] Field of Search ................... 548/495, 454; 514/419

[56] References Cited

U.S. PATENT DOCUMENTS 5,696,146  12/1997  Blagg ........................ 514/414

FOREIGN PATENT DOCUMENTS 458207  11/1991  European Pat. Off. .
9302050  2/1993  WIPO .
9302051  2/1993  WIPO .
9317014  9/1993  WIPO .

*Primary Examiner*—John M. Ford
*Attorney, Agent, or Firm*—Peter C. Richardson; Paul H. Ginsburg; Grover F. Fuller, Jr.

[57] ABSTRACT

A compound of formula (I):

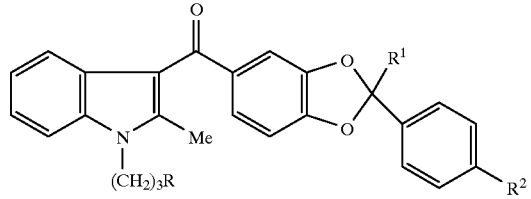

and the pharmaceutically acceptable base salts thereof, wherein: R is $CO_2R^{12}$ where $R^{12}$ is H or a biolabile ester-forming group, or R is tetrazol-5-yl, and either (a) $R^1$ is

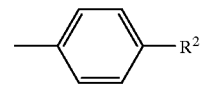

and $R^2$ is F, Cl, Br, I, $CH_3$ or $CF_3$, or (b) $R^1$ is $C_3$–$C_6$ alkyl and $R^2$ is $C_2$–$C_4$ alkyl, useful as steroid 5-α-reductase inhibitors.

9 Claims, No Drawings

INDOLE DERIVATIVES AS 5-α-REDUCTASE-1-INHIBITORS

This is a 371 of PCT/EPA4/02563, filed Aug. 2, 1994.

This invention relates to indole derivatives which have steroid 5α-reductase inhibitory activity.

More particularly this Invention relates to certain 3-[(2,2-disubstituted-1,3-benzodioxolan-5-yl)carbonyl]2-methylindole derivatives, their preparation and their use as testosterone 5α-reductase inhibitors.

The androgen class of steroidal hormones is responsible for the difference In the physical characteristics of males and females. Of all the organs that produce androgens, the testes produce these hormones in the greatest amounts. Overproduction of these hormones in the body results in many undesirable physical manifestations and disease states, e.g. acne vulgaris, alopecia, seborrhoea, female hirsutism, benign prostatic hypertrophy and male pattern baldness.

The principal androgen secreted by the testes is testosterone and it is the primary androgen present in male plasma. The principal mediators of androgenic activity in certain organs such as the prostate and sebaceous glands are the 5α-reduced androgens. Testosterone is therefore the prohormone of 5α-dihydrotestosterone (DHT) which is formed locally in the above organs by the action of testosterone 5α-reductase. The presence of elevated levels of dihydrotestosterone in many disease states has therefore focussed attention on the synthesis of testosterone 5α-reductase inhibitors.

The enzyme 5α-reductase mediates the conversion of testosterone to the more potent androgen DHT locally, in the target organ. It has been postulated, and demonstrated, that inhibitors of 50α-reductase should block the formation of DHT and bring about amelioration of the above undesirable physiological conditions. Testosterone 5α-reductase inhibitors may also be useful in the treatment of human prostate adenocarcinomas. Recently, two 5-α-reductase isozymes (designated types 1 and 2) have been described in humans, Andersson et al., *Proc. Natl. Acad. Sci. U.S.A.*, 87, 3640–3644 (1990; Andersson et al., *Nature*, 354, 159–161 (1991). In addition to certain structural differences, the two isozymes exhibit some differences with respect to their biochemical properties, expression patterns, genetics, and pharmacology, Andersson et al., *Nature*, 354, 159–161 (1991); Jenkins, et al., *Journal of Clinical Investigation*, 89, 293–300 (1992). Further elucidation of the roles that the two 5α-reductase isozymes play In androgen action is currently the subject of intense research. These isozymes are generally described as 5α-reductase 1 or 2, or type 1 or type 2 5α-reductase.

Compounds reportedly useful for inhibiting 5α-reductase are generally steroid derivatives such as the azasterolds in Rasmusson, et al., *J. Med. Chem.*, 29, (11), 2298–2315 (1986); and benzoylaminophenoxy-butanoic acid derivatives such as those disclosed in EPO 291 245.

European Patent Application 0532190 discloses certain benzo[f] quinolinones as 5-α-reductase inhibitors. Certain Indole derivatives having steroid 5-α-reductase inhibitory activity are generally disclosed by International Patent Application No. PCT/EP93/00380 (WO/93/17014).

It has now been surprisingly found that the present compounds are more potent and selective inhibitors of a single isozyme of human testosterone 5α-reductase (i.e. 5α-reductase-1) which leads to the therapeutic advantages that the compounds are more efficacious and that they can be administered at lower doses, in particular for the treatment of male pattern baldness which is known to be primarily responsible for hairloss in the human scalp as well as female hirsutism, acne vulgaris, seborrhea and prostatic cancer.

The present Invention provides compounds of the formula:

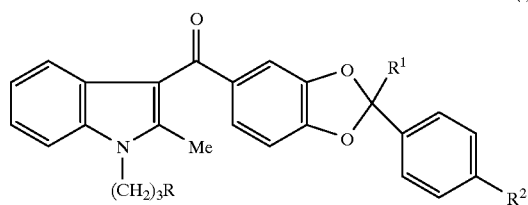

(I)

and the pharmaceutically acceptable base salts thereof, wherein

R is —$CO_2R^{12}$ where $R^{12}$ is H or a biolabile ester-forming group, or R is tetrazol-5-yl, and either (a) $R^1$ is

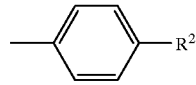

and $R^2$ is F, Cl, Br, I, $CH_3$ or $CF_3$ or (b) $R^1$ is $C_3$–$C_6$ alkyl and $R^2$ is $C_2$–$C_4$ alkyl.

Alkyl groups containing three or more carbon atoms may be straight- or branched-chain.

The term "biolabile ester-forming group" is well understood in medicinal chemistry as meaning a group which forms an ester which can be readily cleaved in vivo to liberate the corresponding compound of the formula (I) where R is —$CO_2H$. A number of such ester groups are well-known, for example In the penicillin area or in the case of the angiotensin-converting enzyme (ACE) inhibitor antihypertensive agents.

The compounds of the formula (I) when $R^{12}$ is a biolabile ester-forming group are not only useful as pro-drugs to provide compounds of the formula (I) wherein R is —$CO_2H$ in vivo following oral administration, but are also useful as intermediates for the preparation of compounds of the formula (I) where R is —$CO_2H$.

The suitability of any particular ester-forming group for this purpose can be assessed by conventional in vitro or In vivo enzyme hydrolysis studies.

Examples of biolabile ester-forming groups are alkyl, alkanoyloxyalkyl (including alkyl, cycloalkyl or aryl substituted derivatives thereof), arylcarbonyloxyalkyl (including aryl substituted derivatives thereof), aryl, arylalkyl, indanyl and haloalkyl: wherein alkanoyl groups have from 2 to 8 carbon atoms, alkyl and haloalkyl groups have from 1 to 8 carbon atoms and aryl means phenyl or naphthyl, both of which may be optionally substituted by $C_1$–$C_4$ alkyl, $C_1$–$C_4$ alkoxy or halo. Alkyl, haloalkyl, alkanoyl and alkoxy groups can, where appropriate, be straight- or branched-chain.

Specific examples of biolabile ester-forming groups are $C_1$–$C_6$ alkyl (e.g. methyl, ethyl, n-propyl, isopropyl), benzyl, 1-(2,2-diethylbutyryloxy)ethyl, 2-ethylproplonyloxymethyl, 1-(2-ethylproplonyloxy)ethyl, 1-(2,4-dimethylbenzoyloxy)ethyl, a-benzoyloxybenzyl, 1-(benzoyloxy)ethyl, 2-methyl-l-propionyloxy-1-propyl, 2,4,6-trimethylbenzoyloxymethyl, 1-(2,4,6-trimethyl-benzoyloxy)ethyl, pivaloyloxymethyl, phenethyl, phenpropyl, 2,2,2-trifluoroethyl, 1- or 2-naphthyl, 2,4-dimethylphenyl, 4t-butylphenyl and 5-indanyl.

The pharmaceutically acceptable base salts of the compounds of the formula (I) are formed from suitable bases which form non-toxic salts and examples thereof are the aluminium, calcium, lithium, magnesium, potassium, sodium, zinc, N-benzyl-N-(2-phenylethyl)amine, 1-adamantylamine and diethanolamine salts.

Preferred base salts are the sodium, potassium, N-benzyl-N-(2-phenylethyl)amine and 1-adamantylamine salts. Sodium salts are the most preferred.

For a review on suitable pharmaceutical salts see Berge et al, Pharm. Sci., 66, 1–19 (1977).

In the above definitions relating to the compounds of the formula (I):

Preferably R is —$CO_2H$.

Preferably $R^1$, when alkyl, is $C_3$–$C_4$ alkyl, more preferably $R^1$ is $C_4$ alkyl, and yet more preferably $R^1$ is n-butyl.

Preferably, when $R^1$ is aryl, $R^2$ is F, Cl, Br or I, more preferably Cl.

Preferably $R^2$, when alkyl, is $C_2$ or $C_3$ alkyl, most preferably ethyl or n-propyl.

A compound of the formula (I) may contain one or more asymmetric carbon atom(s) and therefore exist in two or more stereoisomeric forms. The present invention Includes the individual stereoisomers of the compounds of the formula (I) and mixtures thereof, together, where appropriate, with all the tautomeric forms of the compounds of the formula (I). Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An Individual enantiomer of a compound may also be prepared from a corresponding optically pure Intermediate or by resolution, such as by H.P.L.C. of a racemate using a suitable chiral support or by fractional crystallisation of the diastereoisomeric salts formed by reaction of a racemate with a suitable optically active base.

The compounds of formula (I) provided by the Invention may be prepared by the following methods:

1) The compounds of the formula (I) where R is —$CO_2H$ and $R^1$ and $R^2$ are as previously defined for a compound of the formula (I) may be prepared by cleavage of an ester of the formula:

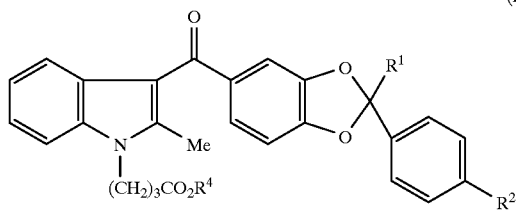

(II)

where $R^4$ is a suitable ester-forming group and $R^1$ and $R^2$ are as previously defined for a compound of the formula (I).

A plethora of suitable ester-forming groups that may be cleaved to provide the corresponding carboxylic acid are known to the skilled person, see, e.g., T. W. Greene, "Protective Groups in Organic Synthesis", Wiley-lnterscience (1981).

Where $R^4$ is an ester-forming group that may be removed by hydrolysis, e.g. a biolabile ester-forming group as previously defined for $R^{12}$ (such as $C_1$–$C_6$ alkyl), the hydrolysis may be carried out under acidic or basic conditions, e.g. using an aqueous solution of either a suitable mineral acid or a suitable inorganic base. Preferably the hydrolysis is carried out under basic conditions.

In a typical hydrolysis procedure, an ester of the formula (II) is treated with an aqueous solution of a suitable base, e.g. sodium or potassium hydroxide, In the presence of a suitable organic co-solvent, e.g. tetrahydrofuran or a $C_1$–$C_4$ alkanol (e.g. methanol or ethanol) or a combination thereof. The hydrolysis is typically carried out at from room temperature to the reflux temperature and preferably at room temperature. The product is obtained as a base salt which may be converted to the carboxylic acid by acidification in the work-up procedure.

Where $R^4$ is an ester-forming group that may be removed by reduction, e.g. benzyl, the reduction may be carried out by catalytic hydrogenation using, e.g. palladium-on-charcoal, as the catalyst.

The compounds of the formula (II) may be prepared by esterification of a compound of the formula (I) where R is —$CO_2H$ with an alcohol of the formula $R^4OH$ where $R^4$ is as previously defined for this method.

The reaction may be carried out under classical esterification conditions such as by using an excess of the alcohol and with acid catalysis, e.g. using sulphuric acid or p-toluenesulphonic acid, at from room temperature to the reflux temperature. The water generated during the reaction may be removed by azeotropic distillation or by the use of a dehydrating agent or a molecular sieve.

The esterification may also be carried out by reacting the acid with the alcohol in the presence of a suitable dehydrating agent, e.g. dicyclohexylcarbodilmide or diethylazodicarboxylate/triphenylphosphine (see O. Mitsunobu, Synthesis, 1981, 1).

Alternatively the esterification may be carried out by first forming an activated ester or imidazolide derivative of the carboxylic acid, followed by reaction of the activated ester or imidazolide in situ with the alcohol of the formula $R^4OH$. An activated ester may be formed by reacting the carboxylic acid with 1-hydroxybenzotriazole in the presence of a suitable dehydrating agent, e.g. 1-(3-N,N-dimethylaminopropyl)-3-ethylcarbodiimide, and in a suitable solvent, e.g. dichloromethane, at room temperature. An imidazolide may be formed by reacting the carboxylic acid with 1,1'-carbonyidilmidazole in a suitable solvent, e.g. dichloromethane, at room temperature.

2) The compounds of the formula (I) where R is —$CO_2H$ and $R^1$ and $R^2$ are as previously defined for a compound of the formula (I) may be prepared by hydrolysis of a compound of the formula:

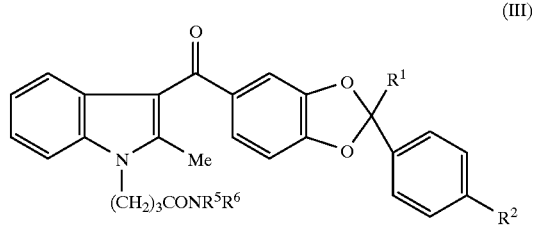

(III)

where $R^5$ and $R^6$ are each Independently selected from H and $C_1$–$C_4$ alkyl and $R^1$ and $R^2$ are as previously defined for a compound of the formula (I).

The hydrolysis may be carried out under acidic or basic conditions, e.g. using an aqueous solution of either a suitable mineral acid (e.g. hydrochloric or sulphuric acid) or a suitable inorganic base (e.g. sodium or potassium hydroxide), at from room temperature to the reflux temperature. When basic hydrolysis conditions are used the product is obtained as a base salt which may be converted to the carboxylic acid by acidification in the work-up procedure.

3) The compounds of the formula (I) wherein R is —CO$_2$H and R$^1$ and R$^2$ are as previously defined for a compound of the formula (I) may be prepared by hydrolysis of a compound of the formula:

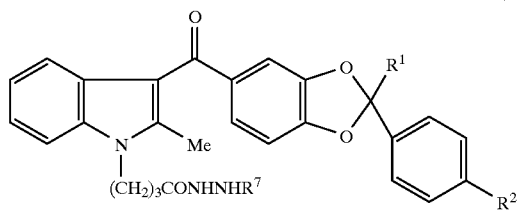

(IV)

where R$^1$ and R$^2$ are as previously defined for a compound of the formula (I) and R$^7$ is H or C$_1$–C$_4$ alkyl.

The hydrolysis may be carried out under acidic or basic conditions, e.g. using an aqueous solution of either a suitable acid (e.g. hydrochloric or acetic acid) or a suitable inorganic base (e.g. sodium or potassium hydroxide), at from room temperature to the reflux temperature. When basic hydrolysis conditions are used the product is obtained as a base salt which may be converted to the carboxylic acid by acidification in the work-up procedure.

4) The compounds of the formula (I) where R is —CO$_2$H and R$^1$ and R$^2$ are as previously defined for a compound of the formula (I) may be prepared by hydrolysis of a compound of the formula:

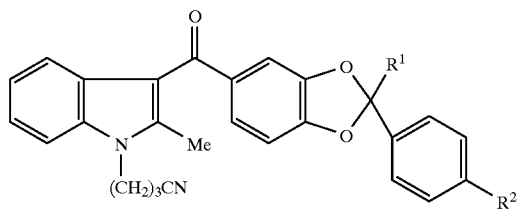

(V)

where R$^1$ and R$^2$ are as previously defined for a compound of the formula (I).

The hydrolysis may be carried out under acidic or basic conditions, e.g. using an aqueous solution of either a suitable acid (e.g. hydrochloric or sulphuric acid) or a suitable inorganic base (e.g. sodium or potassium hydroxide), at from room temperature to the reflux temperature. When basic conditions are used hydrogen peroxide may optionally be present and also the product is obtained as a base salt which may be converted to the carboxylic acid by acidification In the work-up procedure.

5) The compounds of the formula (I) where R is —CO$_2$H and R$^1$ and R$^2$ are as previously defined for a compound of the formula (I) may be prepared by acidic hydrolysis of a compound of the formula:

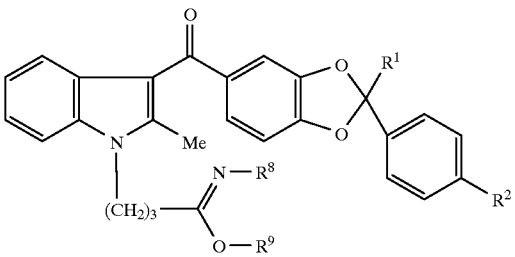

(VI)

where R$^1$ and R$^2$ are as previously defined for a compound of the formula (I) and R$^8$ and R$^9$ taken together represent ethylene, said ethylene being optionally substituted by phenyl or C$^1$–C$_4$ alkyl (preferably methyl). Preferably R$^8$ and R$^9$ taken together represent —CH$_2$C(CH$_3$)$_2$—.

The hydrolysis may be carried out using an aqueous solution of a suitable acid such as hydrochloric acid at from room temperature to the reflux temperature.

6) All the compounds of the formula (I) may be prepared by alkylation of a base salt (i.e. the N-deprotonated form) of a compound of the formula:

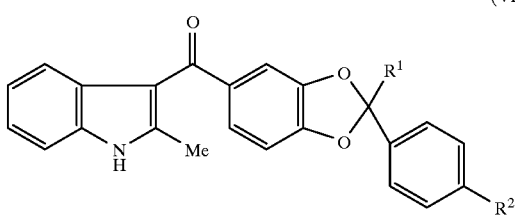

(VII)

where R$^1$ and R$^2$ are as previously defined for a compound of the formula (I), with a compound of the formula:

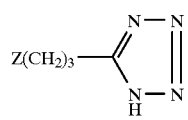

(VIII)

or a base salt thereof, or with a base salt of a compound of the formula Z(CH$_2$)$_3$—CO$_2$H, where Z is a suitable leaving group, e.g. halo (preferably bromo or iodo), methanesulphonyloxy or p-toluenesulphonyloxy.

The preferred base salts of the compounds of the formula Z(CH$_2$)$_3$—CO$_2$H include the alkali metal and alkaline earth metal salts, e.g. the sodium and potassium salts.

The preferred base salts of the compounds of the formulae (VII) and (VIII) include the alkali metal salts, e.g. the sodium and potassium salts.

The reaction may be performed by initial deprotonation of a compound of the formula (VII) with a suitable base, e.g. sodium hydride or potassium carbonate, followed by reaction of the resulting anion with a compound of the formula (VIII) or a base salt thereof, or with a base salt of a compound of the formula Z(CH$_2$)$_3$—CO$_2$H, as appropriate. The reaction may be carried out in a suitable solvent, e.g. N,N-dimethylformamide, tetrahydrofuran or 2-butanone, at from 0° C. to the reflux temperature.

Alternatively the reaction may be carried out under phase transfer conditions using a suitable base such as sodium or potassium hydroxide.

The compound of the formula (I) may be obtained as a base salt which can be converted to the carboxylic acid or NH-tetrazole, as appropriate, by acidification in the work-up procedure.

7) The compounds of the formula (I) where R is —$CO_2H$ and $R^1$ and $R^2$ are as previously defined for a compound of the formula (I) may be prepared by oxidative cleavage of a compound of the formula:

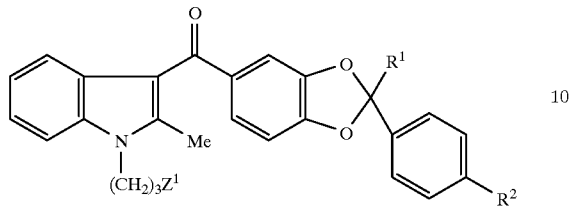
(IX)

where $Z^1$ is —$CH=CH_2$ or —$C\equiv CH$ and $R^1$ and $R^2$ are as previously defined for a compound of the formula (I).

The reaction may be carried out by ozonolysis or by treatment with aqueous potassium permanganate solution.

8) The compounds of the formula (I) wherein R is —$CO_2H$ and $R^1$ and $R^2$ are as previously defined for a compound of the formula (I) may be prepared by oxidation of a compound of the formula:

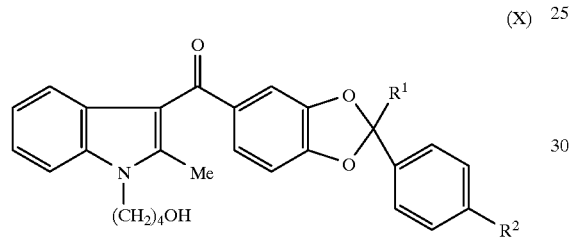
(X)

where $R^1$ and $R^2$ are as previously defined for a compound of the formula (I). A suitable oxidising agent for this purpose is chromium trioxide in pyridine.

9) All the compounds of the formula (I) may be prepared by reaction of a compound of the formula:

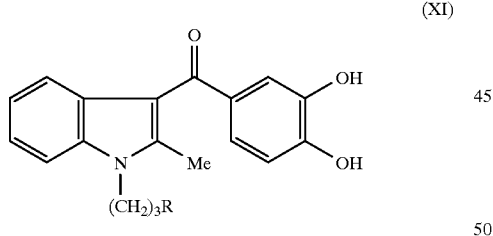
(XI)

where R is as previously defined for a compound of the formula (I), with a) a compound of the formula:

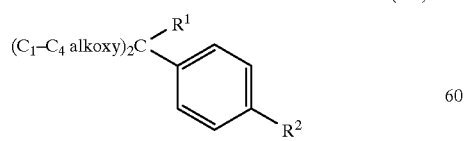
(XII)

where $R^1$ and $R^2$ are as previously defined for a compound of the formula (I). In a typical procedure the ketal of the formula (XII) and the compound of the formula (XI) are heated together under reflux in a suitable organic solvent, e.g. toluene, in the presence of a catalytic amount of a suitable acid, e.g. p-toluenesulphonic acid. Preferably a dimethyl ketal is used and the reaction is carried out in a Dean-Stark apparatus;

b) a compound of the formula:

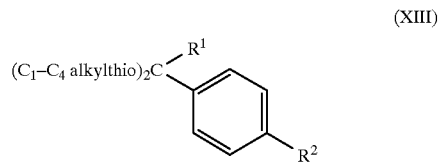
(XIII)

where $R^1$ and $R^2$ are as previously defined for a compound of the formula (I). The preferred $C_1$–$C_4$ alkyl group In the compounds of the formula (XIII) is methyl. In a typical procedure the compounds of the formula (XI) and (XIII) are heated together in a suitable organic solvent, e.g. toluene, with mercury (II) catalysis, e.g. using mercury (II) chloride;

c) a compound of the formula:

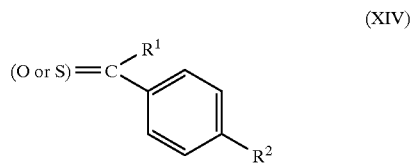
(XIV)

where $R^1$ and $R^2$ are as previously defined for a compound of the formula (I). In a typical procedure the compounds of the formulae (XI) and (XIV) are heated together under reflux in a suitable organic solvent, e.g. toluene, In the presence of a suitable acid catalyst, e.g. hydrochloric acid or sulphuric acid, and preferably in a Dean-Stark apparatus; or d), for compounds of the formula (I) where the $R^1$ moiety is alkyl having hydrogen atom on the α-carbon atom with 20 respect to its position of attachment to the 1,3-benzodioxolane ring, an enol ether derivative of a compound of the formula:

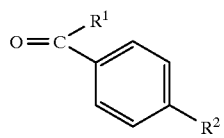
(XIV A)

where $R^1$ and $R^2$ are as previously defined for a compound of the formula (I) but with the above condition applying in respect of the definition of $R^1$. The reaction is typically carried out in a suitable organic solvent, e.g. toluene, in the presence of an acid catalyst, e.g. p-toluenesulphonic, hydrochloric or sulphuric acid, at from room temperature to the reflux temperature of the solvent.

Suitable enol ether derivatives for use in this procedure (d) may be derived from a compound of the formula (XIVA) by reaction with a suitable tri($C_1$–$C_4$ alkyl) orthoformate, e.g. trimethyl orthoformate, in the presence of an acid catalyst, e.g. p-toluenesulphonic acid.

To prepare a compound of the formula (I) any one of methods (9)(a) to (d) may also be carried out using a suitable base (e.g. sodium) salt of a compound of the formula (XI), e.g. where R is —CO₂H, a carboxylate salt, the reaction being followed by an acidification step in the work-up procedure, as appropriate. The starting materials of the formula (XI) may be prepared by acidic hydrolysis of a compound of the formula:

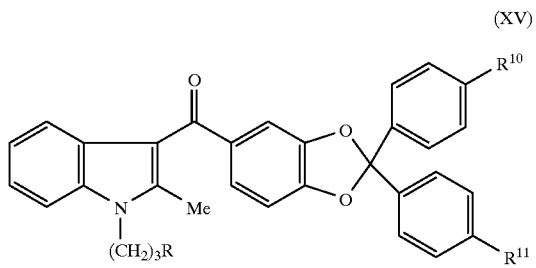

(XV)

where R¹⁰ and R¹¹ are each independently selected from H and Cl and are preferably both Cl, and R is as previously defined for a compound of the formula (I).

In a typical procedure the hydrolysis is carried out using aqueous acetic acid and the reaction is heated under reflux.

The compounds of the formula (XV) may be prepared by similar methods to those described herein for the preparation of the compounds of the formula (I).

10) The compounds of the formula (I) where R is tetrazol-5-yl and R¹ and R² are as previously defined for a compound of the formula (I), may be prepared by reaction of a compound of the formula (V) where R¹ and R² are as previously defined for a compound of the formula (I), with a suitable azide, e.g. an alkali metal azide (preferably sodium azide) or trimethylsilylazide in the presence of fluoride ion. The reaction is typically carried out in a suitable solvent, e.g. N-methyl-2-pyrrolidinone, at from 100 to 150° C. (see Synthesis, 1987, 1133).

11) The compounds of the formula (I) where R is tetrazol-5-yl and R¹ and R² are as previously defined for a compound of the formula (I), may be prepared by deprotection of a compound of the formula:

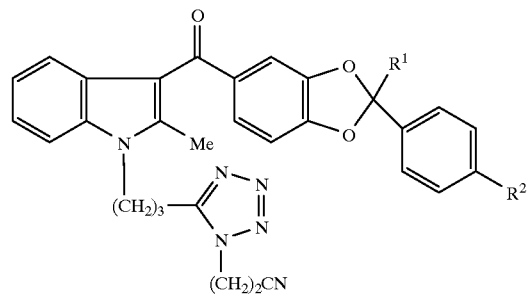

(XVI)

where R¹ and R² are as previously defined for a compound of the formula (I).

In a typical procedure the deprotection is carried out using a suitable base, e.g. sodium hydroxide, and in a suitable solvent, e.g. tetrahydrofuran methanol, at about room temperature.

A compound of the formula (XVI) may be prepared by a two-step procedure starting from the corresponding compound of the formula (I) where R is —CO₂H and R¹ and R² are as previously defined for a compound of the formula (I). In the first step the carboxylic acid is reacted with 3-aminopropanitrile under standard peptide coupling conditions, e.g. using 1-(3-N,N-dimethylaminopropyl)-3-ethylcarbodiimide and 1-hydroxybenzotriazole in a suitable solvent such as dichloromethane, to provide a compound of the formula:

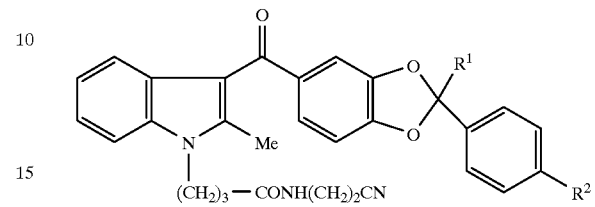

(XVII)

where R¹ and R² are as previously defined for a compound of the formula (I).

A compound of the formula (XVII) may be converted to a compound of the formula (XVI) by treatment with trimethylsilylazide, diethylazodicarboxylate and triphenylphosphine in a suitable solvent, e.g. tetrahydrofuran, at room temperature.

This method of converting a compound of the formula (I) where R is —CO₂H to a compound of the formula (I) where R is tetrazol-5-yl is based on a literature procedure that is described in J. Org. Chem., 56, 2395 (1991).

The compounds of the formulae (II), (III), (IV), (V), (VI), (IX), (X), (XVI) and (XVII) can all be prepared by appropriate alkylation of a base salt of a compound of the formula (VII) by a similar procedure to that described in method (6) for the preparation of the compounds of the formula (I).

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable base salt of a compound of the formula (I) may be readily prepared by mixing together solutions of a compound of the formula (I) and the desired base. The salt may precipitate from solution and be collected by filtration or may be recovered by evaporation of the solvent.

The compounds of the formula (I) are steroid 5α-reductase inhibitors and therefore they are useful in the curative or prophylactic treatment of diseases or conditions such as acne vulgaris, alopecia, seborrhoea, female hirsutism, benign prostatic hypertrophy and male pattern baldness.

The compounds of the formula (I) are also useful for the treatment of human prostate adenocarcinomas.

The compounds of the formula (I) may be tested in vitro for testosterone 5α-reductase inhibitory activity using prostate tissue from rats or humans as follows:

(a) The compounds of the formula (I) may be tested for their potency in inhibiting rat testosterone 5α-reductase using ventral prostate tissue from male rats. In determining inhibitory potency against rat prostatic 5α-reductase the following procedure was employed:

Rat prostates were minced into small pieces. The tissue was homogenised in Buffer A (20 mM sodium phosphate, pH 6.5, buffer containing 0.32M sucrose and 1 mM dithiothreitol) with a Brinkman Polytron (Kinematica GmBH, Luzern), and then homogenised with a motor-driven (1000 rpm) Potter Elvehjem (teflon-to-glass) homogeniser. Prostate particles were obtained by centrifugation at 105,000 G for 60 minutes. The pellet was washed in 4 volumes of Buffer A and recentrifuged at 105,000 G. The resulting pellet was dispersed in Buffer A (1 ml per g of prostate tissue originally used) with a motor-driven Potter Elvehiem homogeniser as described above. The particulate suspension was stored as 1 ml samples at −70° C.

The following components, dissolved in Buffer B (40 mM sodium phosphate buffer, pH 6.5), were added to a test tube: 500 1 of [$^3$H]-testosterone (1 $\mu$ci, 1 nmol; Du Pont, NEN Research Products, Stevenage, U.K.), 100 $\mu$l of 0.5 mM NADPH, a compound of the formula (I) dissolved in 5 $\mu$l of dimethyl sulphoxide, and Buffer B to give a final reaction volume of 1 ml. The mixture was warmed to 37° C. and the reaction started by addition of an aliquot of prostate particulate suspension. The reaction mixture was incubated at 37° C. for 30 minutes and then quenched by addition with vigorous mixing of 2 ml of ethyl acetate containing 20 $\mu$g each of testosterone and 5$\alpha$-dihydrotestosterone as carriers. The aqueous and organic layers were separated by centrifugation at 2000 G for 10 minutes. The organic layer was transferred to a second test tube and evaporated to dryness under nitrogen. The residue was dissolved in 50–80 $\mu$l of absolute ethanol, spotted onto a silica gel 60 F254 TLC plate (E. Merck, Darmstadt, Germany) and developed in dichloromethane:acetone (185:15).

The radiochemical content in the bands of the substrate (testosterone) and the product (5$\alpha$-dihydrotestosterone) were determined with a RITA Radio TLC Analyser (Raytest Instruments Ltd., Sheffield, U.K.). The percent of recovered radiolabel converted to 5$\alpha$-dihydrotestosterone was calculated and used to determine enzyme activity. All incubations were conducted so that no more than 15% of substrate (testosterone) was converted to product.

The experimentally obtained data for a range of inhibitor concentrations was omputer fitted to a sigmoidal dose-response curve and concentrations of compound giving 50% inhibition of 5$\alpha$-reductase activity (IC$_{50}$'s) were calculated using a SIGFIT program (De Lean, A., Munson, P. J. and Rodbard, D., American Journal of Physiology, 235, E97 (1978)).

(b) (i) The compounds of the formula (I) may be tested for their potency in inhibiting human testosterone 5$\alpha$reductase-2 using tissue from hyperplastic human prostates. In determining inhibitory potency against human prostatic 5$\alpha$-reductase-2 the following procedure was employed:

Frozen human prostate tissue was puiverised in liquid nitrogen using a steel mortar and pestle. The powdered tissue was homogenised in 4 volumes of Buffer A (20 mM sodium phosphate, pH 6.5, containing 0.32M sucrose, 1 mM dithiothreitol and 50 $\mu$M NADPH) with an Ultra-Turrax homogeniser (Janke and Kunkel GmBH & Co., Staufen I.BR., Germany). The homogenate was centrifuged at 500 G for 5 minutes to remove large particles of tissue, and the supernatant was then centrifuged at 100,000 G for 1 hour. The resulting pellet was dispersed in Buffer A (1 ml per g of prostate tissue originally used) with the Ultra-Turrax homogeniser. This particulate preparation was then filtered through 2 layers of cheesecloth and the filtrate was stored as 2 ml samples at −70° C.

The following components, dissolved in Buffer B (25 mM citrate phosphate buffer, pH 5.2), were added to a test tube: 100 $\mu$l of [$^3$H]-testosterone (1 $\mu$Ci, 1nmol; Du Pont, NEN Research Products, Stevenage, U.K.), 100 $\mu$l of NADPH regeneration system (5 mM NADPH, 50 mM glucose 6-phosphate, 5 units/ml glucose 6-phosphate dehydrogenase), a compound of the formula (I) dissolved in 5 $\mu$l of dimethyl sulphoxide, and Buffer B to give a final reaction volume of 1 ml. The mixture was warmed to 37° C. and the reaction started by addition of an aliquot of prostate particulate suspension. The reaction mixture was incubated at 37° C. for 30 minutes and was then quenched by addition, with vigorous mixing, of 2 ml of ethyl acetate containing 20 $\mu$g each of testosterone and 5$\alpha$-dihydrotestosterone as carriers. The aqueous and organic layers were separated by centrifugation at 2000 G for 10 minutes. The organic layer was transferred to a second test tube and evaporated to dryness under nitrogen. The residue was dissolved in 50–80 $\mu$l of absolute ethanol, spotted onto a silica gel 60 F254 TLC plate (E. Merck, Darmstadt, Germany) and developed in dichloromethane:acetone (185:15).

The radiochemical content in the bands of the substrate (testosterone) and the product (5$\alpha$-dihydrotestosterone) were determined with a RITA Radio TLC Analyser (Raytest Instruments Ltd., Sheffield, U.K.). The percent of recovered radiolabel converted to 5$\alpha$-dihydrotestosterone was calculated and used to determine enzyme activity. All incubations were conducted so that no more than 15% of substrate (testosterone) was converted to product.

The experimentally obtained data for a range of inhibitor concentrations was computer fitted to a sigmoldal dose-response curve and concentrations of compound giving 50% inhibition of 5$\alpha$-reductase activity (IC$_{50}$'s) were calculated using a SIGFIT program (De Lean, A., Munson, P. J. and Rodbard, D., American Journal of Physiology, 235 E97 (1978)).

(ii) The compounds of the formula (I) may be tested for potency in inhibiting steroid 5$\alpha$-reductase activity in human prostate adenocarcinomas using cell lines DU145 and HPC36M. In determining inhibitory potency against 5$\alpha$-reductase the following procedure was employed:—Human prostate adenocarcinoma cell lines were grown in Dulbecco's Modified Eagles medium (DMEM) containing 5% serum. The cells were recovered from the medium by centrifugation, washed in serum-free DMEM and suspended at 5–10×10$^6$ cells/ml. in serum-free medium.

The following components were added to a test tube: 10 $\mu$l of [$^3$H]-testosterone (1 $\mu$Ci, 20 pmol) dissolved in ethanol (Du Pont, NEN Research Products, Stevenage, U.K.) and 5 $\mu$l of an ethanol solution of a compound of the formula (I). The ethanol was evaporated under nitrogen and the testosterone and the compound were redissolved in 0.25 ml of serum-free medium containing 0.25 $\mu$mol NADPH. The mixture was warmed to 37° C. and the reaction started by addition of 0.25 ml of cell suspension (1.2–2.5×10$^6$ cells). The reaction mixture was incubated at 37° C. for 2 hours and then quenched by addition, with vigorous mixing, of 1.5 ml of ethyl acetate containing 20 $\mu$g each of testosterone and 5$\alpha$-dihydrotestosterone as carriers.

The aqueous and organic layers were separated by centrifugation at 2000 G for 10 minutes. The organic layer, containing testosterone and its metabolites, was transferred to a second test tube and evaporated to dryness under nitrogen. The residue was dissolved in 50–80 $\mu$l of absolute ethanol, spotted onto a silica gel 60 F254 TLC plate (E. Merck, Darmstadt, Germany) and developed in dichloromethane: acetone (185:15).

The radiochemical content in the bands of the substrate (testosterone) and the product (5$\alpha$-dihydrotestosterone) was determined with a RITA Radio TLC Analyser (Raytest Instruments Ltd., Sheffield, U.K.). The percentage of recovered radiolabel converted to 5$\alpha$-dihydrotestosterone was calculated and used to determine enzyme activity. All incubations were conducted so that no more than 15% of substrate (testosterone) was converted to product.

The experimentally obtained data for a range of inhibitor concentrations was computer fitted to a sigmoidal dose-response curve and concentrations of compound giving 50% inhibition of 5α-reductase activity ($IC_{50}$'s) were calculated using a SIGFIT program (De Lean, A., Munson, P. J. and Rodbard D., American Journal of Physiology, 235, E97 (1978)).

The compounds of the formula (I) may be tested in vitro for human testosterone 5α-reductase-1 inhibitory activity using cloned human testosterone 5α-reductase-1 according to the procedure described in Proc. Natl. Acad. Sci. USA, 87, 3640 (1990).

For human use, the compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) will be from 0.01 to 20 mg/kg (in single or divided doses) and preferably will be from 0.1 to 10 mg/kg except for the treatment of human prostate adenocarcinomas where doses of up to 20 mg/kg may be used. Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) may also be administered together with an α-antagonist (e.g. prazosin or doxazosin), an antiandrogen (e.g. flutamide) or an aromatase inhibitor (e.g. atamestane), particularly for the curative or prophylactic treatment of benign prostatic hypertrophy.

The following Examples illustrate the preparation of the compounds of the formula (I):

EXAMPLE 1

4-[3-([2,2-p-Chlorophenyl-1,3-benzodioxolan-5-yl] carbonyl)-2-methylindol-1-yl]butanoic acid.

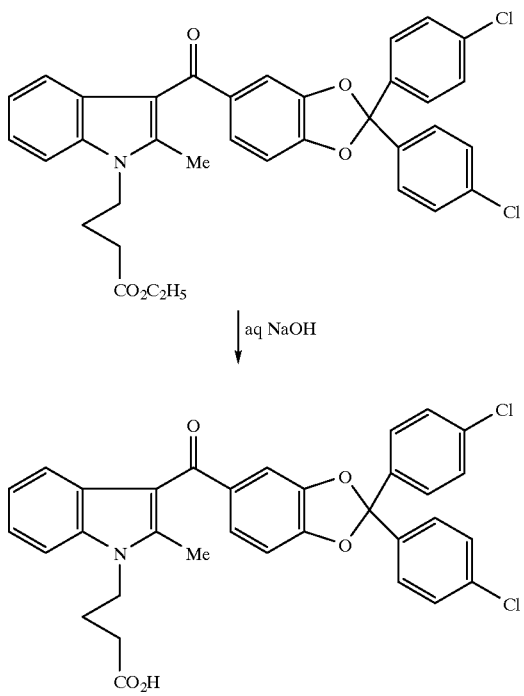

A solution of ethyl-4-[3-([2,2-p-chlorophenyl-1,3-benzodioxolan-5-yl]carbonyl)-2-methylindol-1-yl] butanoate (685 mg) (see Example 4) in tetrahydrofuran (10 ml) and methanol (10 ml) was treated with 2N aqueous sodium hydroxide (10 ml) and stirred overnight (25° C.). The mixture was concentrated in vacuo, cooled in an ice bath and acidified with 2N aqueous hydrochloric acid. The acid phase was extracted with ethyl acetate (50 ml), the organic extract dried ($MgSO_4$), filtered and evaporated in vacuo to give the title compound as a yellow foam (550 mg). Found: C,66.84; H,4.59; N,2.17; $C_{33}H_{25}Cl_2NO_5$ requires: C,67.58; H,4.30; N,2.39%. m/z=588(m+) and 586(m+). $^1$H-NMR ($CDCl_3$):δ=2.15(m,2H), 2.50(t,2H), 2.60(s,3H), 4.25(t,2H), 6.85(d, 1H), 7.10(t,1H), 7.25(t,1H), 7.35–7.55 (m,12H) ppm.

EXAMPLE 2

4-[3-([2-butyl-(4-n-propylphenyl)-1.3-benzodioxolan-5-yl ]carbonyl)2-methylindol-1-yl] butanoic acid The procedure of Example 1 was followed but using ethyl-4-[3-([2-butyl-2(4-n-propylphenyl)-1,3-benzodioxolan-5-yl]carbonyl)2-methylindol-1-yl]butanoate (from Example 5) as the starting material to give the title compound as a white foam: Found: C,74.94; H,6.81; N,2.33; $C_{34}H_{37}NO_5$ requires: C,75.67; H,6.91; N,2.60%. m/z=540 (m+). $^1$H-NMR ($CDCl_3$):δ=0.95(t,3H), 1.00(t,3H), 1.30–1.55(m,4H), 1.65(m,2H) 2.20(m,2H), 2.30(m,2H), 2.55(t,2H), 2.60(t,2H), 2.65(s,3H), 4.25(t,2H), 6.80(d, 1H), 7.10(t, 1H), 7.20–7.55(m,9H) ppm.

EXAMPLE 3

4-[3-([2-butyl-2-(4-ethylphenyl)-1,3-benzodioxolan-5-yl]carbonyl)2-methylindol-1-yl]butanoic acid The procedure of Example 1 was followed but using ethyl-4-[3-([2-butyl-2-(4-ethylphenyl)-1,3-benzodioxolan-5-yl]carbonyl)2-methylindol-1-yl]butanoate (from Example 6) as starting material to give the title compound as a white foam: Found: C,74.41; H,6.88; N,2.36; $C_{33}H_{35}NO_5 \cdot \frac{1}{2}H_2O$ requires C,74.12; H,6.79; N,2.62%. m/z=526(m+1). $^1$H-NMR (CDCl$_3$): δ=0.90(t,3H), 1.25(t,3H), 1.28–1.50(m, 4H), 2.15–2.20(m,2H), 2.20–2.28(m,2H), 2.49(t,2H), 2.60 (s,3H), 2.65(q,2H), 4.25(t,2H) 6.80(d, 1H), 7.10(t, 1H), 7.20–7.55(m,9H) ppm.

EXAMPLE 4

Ethyl-4-[3-([2.2-p-chlorophenyl-1.3-benzodioxolan-5-yl]carbonyl)2-methylindol-1 -yl]butanoate

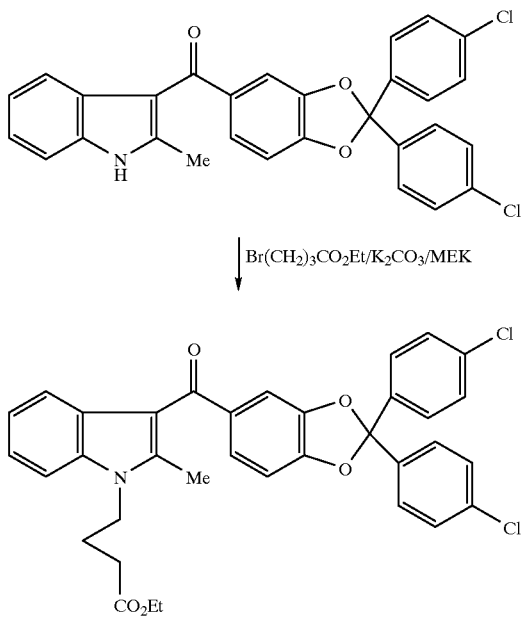

A suspension of 3-([2,2-p-chlorophenyl-1,3-benzodioxolan-5-yl]carbonyl)2-methylindole (9.0 g) (see Preparation 1) in 2-butanone was treated with anhydrous potassium carbonate (24.84 g) and ethylbromobutyrate (3.35 ml). The mixture was mechanically stirred and heated under reflux for 16 hours. After cooling, the mixture was filtered and the filtrate evaporated to an oil. Flash column chromatography SiO$_2$ (3:1 hexane/ethylacetate) gave the title compound as a white foam (6.0 g). m/z=614 (m+) and 616 (m+). $^1$H-NMR (CDCl$_3$): δ=1.30(t,3H), 2.15(m,2H), 2.40(t,2H), 2.60(s, 3H), 4.15(q,2H),4.25(t,2H),6.90(d,1 H), 7.1 0(t,1 H),7.20(t,1 H),7.35–7.55(m,12H) ppm.

EXAMPLE 5

Ethyl-4-[3-(r2-butyl-2-W4-n-propylphenyl)-1.3-benzodioxolan-5-yl]carbonyl)2-methylindol-1-yl] butanoate

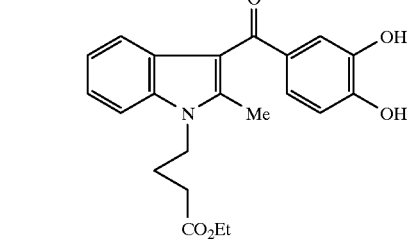

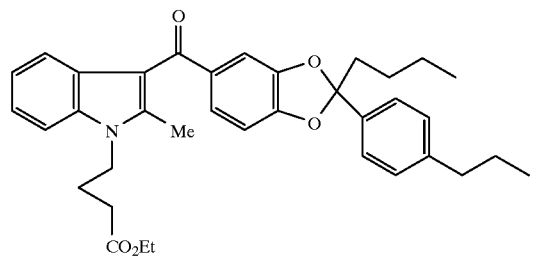

A mixture of ethyl-4[3-(3,4-dihydroxybenzoyl)2-methylindol-1-yl]butanoate (320 mg) (see Preparation 2) and 1,1-dimethoxy-1-(4-n-propylphenyl)pentane (580 ml) (see Preparation 5) in toluene (40 ml) was treated under reflux (1 hour) in a Dean and Stark apparatus. The first few millilitres of toluene were collected and removed, the reaction cooled (60° C.) and p-toluenesulphonic acid (30 mg) added to the reaction mixture. The mixture was heated under reflux (16 hour), cooled and evaporated. Flash column chromatography SiO$_2$ (3:1 hexane/ethyl acetate) gave the title compound as a clear oil (380 mg). m/z=554 (m+). $^1$H-NMR (CDCl$_3$): δ=0.90(t,3H), 1.25(t,3H), 1.28(t,3H), 1.30-1.50(m,6H) 2.10(m,2H), 2.20–2.30(m,2H), 2.40(t,2H), 2.60(s,3H), 2.65–2.75(m,2H), 4.15(q, 2H), 4.20(t,2H), 6.80 (d,1H), 7.07(t,1H), 7.17–7.40(m,7H), 7.50(d,2H) ppm.

EXAMPLE 6

Ethyl-4-r3-(r2-butyl-2(4-ethylphenyl)-31-benzodioxolan-5-yllcarbonyl)2-methylindol-1 -yl] butanoate The procedure of Example 5 was followed but using 1,1-dimethoxy-1-(4-ethylphenyl)pentane, in place of 1,1-dimethoxy-1-(4-n-propylphenyl)pentane, to give the title compound as a clear oil. m/z=554(m+). $^1$H-NMR (CDCl$_3$): δ=0.90(t,3H), 1.25(t,3H), 1.28(t,3H), 1.30–1.50(m,4H 2.15–2.20(m,2H), 2.20–2.28(m,2H), 2.49(t,2H), 2.60(s,3H), 2.65(q,2H), 4.15(q,2H), 4.25(t,2H), 6.80(d,1 H), 7.10(t,1 H), 7.20-7.55(m,7H), 7.60(d,2H) ppm.

PREPARATION 1

3-([2.2-p-chlorophenyl-1.3-benzodioxolan-5-yl]carbonyl)2-methylincdole

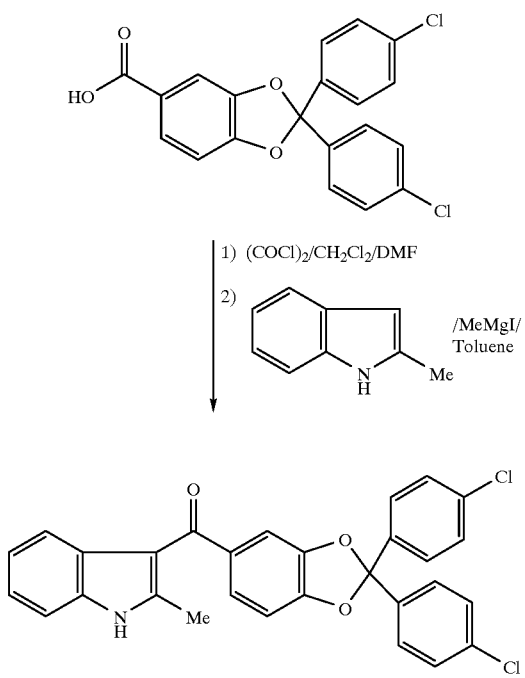

2,2-p-chlorophenyl-1,3-benzodioxolan-5-carboxylic acid (9.70 g) (from Preparation 3) was suspended in dichloromethane (200 ml) and treated with oxalyl chloride (2.6 ml) and dimethylformamide (7 drops). The mixture was stirred (1 hour) until homogenous and then evaporated to a cream solid which was azeotroped (×3) with toluene to remove oxalyl chloride. The crude acid chloride was used directly in the next stage.

A solution of 2-methylindole (6.56 g) in toluene (50 ml) was treated with methylmagnesium iodide (16.7 ml of 3.0M solution in diethyl ether) and cooled to −78° C. Pyridine (4.0 ml) was added followed by portionwise addition of the acid chloride prepared as above; the mixture was allowed to warm to room temperature overnight and then partitioned between ethyl acetate and saturated aqueous ammonium chloride solution. The organic layer was separated and concentrated slightly. Upon standing overnight the title compound crystallised as a pink solid. Filtration and trituration with 9:1 hexane/ethyl acetate gave the title compound as a pale pink powder (9.0g). m/z=500 (m+). $^1$H-NMR (d$^6$-DMSO): δ=2.40(s, 3H), 7.00(t,1 H), 7.10–7.40(m,6H), 7.55–7.60(m,8H),11.90(s,br,1 H) ppm.

PREPARATION 2

Ethyl-4[3-(3.4-dihydroxybenzoyl)2-methylindol-1-yl]butanoate

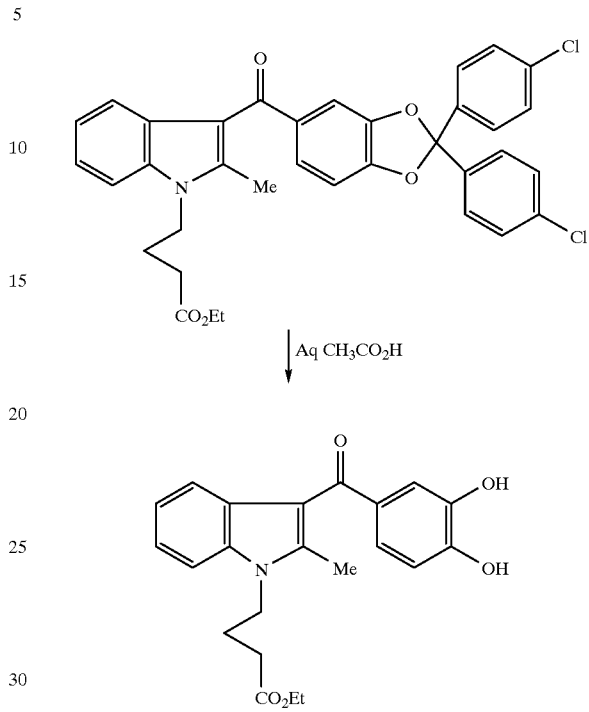

Ethyl-4-[3-([2,2-p-chlorophenyl-1,3-benzodioxolan-5yl]carbonyl)2-methylindol-1-yl]butanoate (4.5 g) was dissolved in glacial acetic acid (80 ml) and water (70 ml) and heated under reflux for 8 hours. The reaction mixture was cooled, evaporated in vacuo and the residue partitioned between ethyl acetate and saturated aqueous sodium bicarbonate. The organic layer was separated and washed (×3) with saturated aqueous sodium bicarbonate. The organic layer was dried (MgSO$_4$) and evaporated to give the title compound as a tan solid (1.52 g). m/z=382(m+1). $^1$H-NMR (CDCl$_3$): δ=1.10(6,3H), 1.85–1.95(m,2H), 2.35–2.45(m, 2H), 2.45(s,3H), 4.00(q,2H), 4.25(t,2H), 6.80(d,2H), 6.95–7.40(m,4H), 7.50(d,1H), 9.40(s,br, 2H) ppm.

PREPARATION 3

2,2-p-Chlorophenyl-1,3-benzodioxolan-5-carboxylic acid

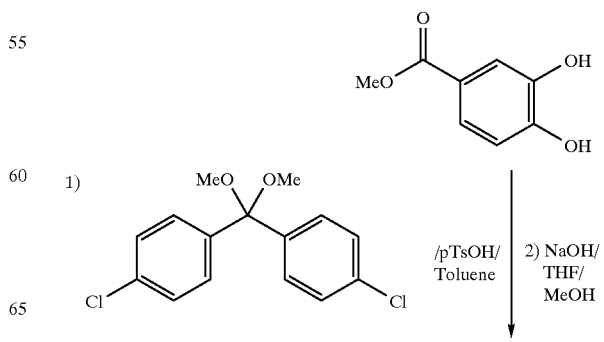

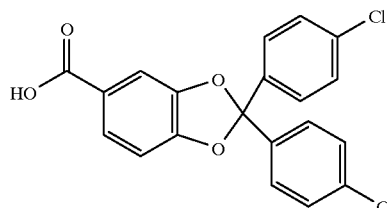

A mixture of 4,4'-dichlorobenzophenone dimethylketal (8.71 g) (Preparation 4) and 3,4-dihydroxymethylbenzoate (5.19 g) in toluene (200 ml) was heated under reflux (1 hour) in a Dean and Stark apparatus. After cooling (60° C.), p-toluenesulphonic acid (50 mg) was added and the mixture heated under reflux overnight. Upon cooling, the mixture was evaporated to a red gum which was dissolved in methanol (60 ml) and tetrahydrofuran (60 ml) at 0°; 2N aqueous sodium hydroxide (60 ml) was added and the mixture stirred overnight. Careful evaporation of the methanol and tetrahydrofuran was followed by addition of 2N aqueous hydrochloric acid until the mixture became acidic. The resultant precipitate was collected and dried to give the title compound as an off-white powder (7.15 g). m/z=386 (m+) and 388 (m+). $^1$H-NMR (d$^6$-DMSO): δ=7.00(d, 1H), 7.40(s, 1H), 7.45–7.55(m,9H) ppm.

PREPARATION 4

4,4'-Dichlorobenzophenone dimethyl ketal

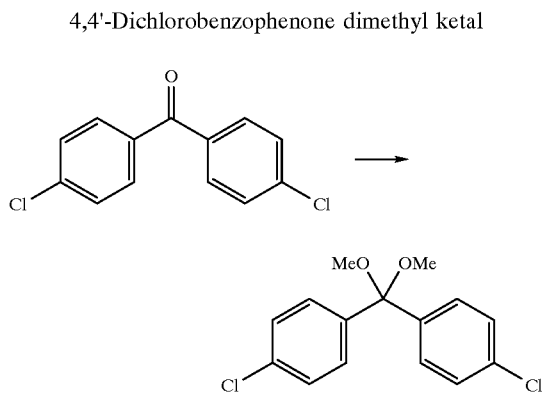

A mixture of 4,4-dichlorobenzophenone (20.0 g), trimethylortholormate (20.0 ml), methanol (200 ml) and p-toluene sulphonic acid (100 mg) was heated under reflux (16 hours). The cooled reaction was evaporated and basified with a few drops of 30% w/w solution of sodium methoxide in methanol; at this point the product crystallised out as chunky needles. Filtration gave the title compound as a crystalline solid (22.0g). m/z=296 (m+). $^1$H-NMR (CDCl$_3$): δ=3.10(s,6H), 7.30(d,4H), 7.40(d,4H) ppm.

PREPARATION 5

1,1-Dimethoxy-1-(4-n-propyl)phenylpentane

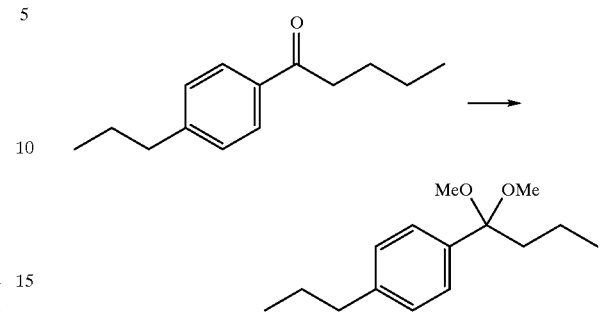

A mixture of 1-(4-n-propyl)phenylpentan-1-one (500 mg) (see Preparation 6), trimethyl orthoformate (1.1 ml), methanol (20 ml) and p-toluenesulphonic acid (10 mg) was heated under reflux for 16 hours. The cooled reaction mixture was basified (using a few drops of a 30% w/w solution of sodium methoxide in methanol) and the reaction mixture was partitioned between water (20 ml) and diethyl ether (20 ml). The ether layer was separated, washed with brine (20 ml) and dried (MgSO$_4$) to give the title compound as a colourless oil (600 mg). $^1$H-NMR (CDCl$_3$): δ=1.80(t,3H), 0.90–1.02(m,5H), 1.10–1.25(m,2H), 1.60-1.75(m,2H), 1.85–1.92(m,2H), 2.60(t,2H), 3.17(s,6H), 7.17(d,2H), 7.36 (d,2H) ppm.

PREPARATION 6

1-(4-n-Propyl)phenylpentan-1-one

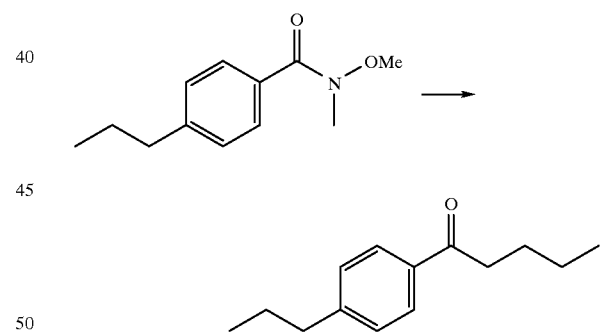

A solution of n-butyl lithium (1.6N in hexane, 3.65 ml) in tetrahydrofuran (10 ml) was cooled to −78° C., treated dropwise with a solution of N-methoxy-N-methyl-4-n-propylbenzamide (1.1 g) (see Preparation 7) in tetrahydrofuran (10 ml) and the solution was allowed to warm to room temperature overnight. The reaction mixture was partitioned between dichloromethane (50 ml) and 2N aqueous hydrochloric acid (50 ml). The organic layer was separated, dried (MgSO$_4$) and evaporated to give a yellow oil which was subjected to flash chromatography (silica, eluant=3:1 hexane/ethyl acetate) to give the title compound as a clear oil (545 mg). $^1$H-NMR (CDCl$_3$): δ=0.95(t,6H), 1.38–1.49(m, 2H), 1.62–1.80(m,4H), 2.65(t,2H), 2.95(t,2H), 7.25(d,2H), 7.90(d,2H) ppm.

PREPARATION 7

N-Methoxy-N-methyl-4-n-propylbenzamide

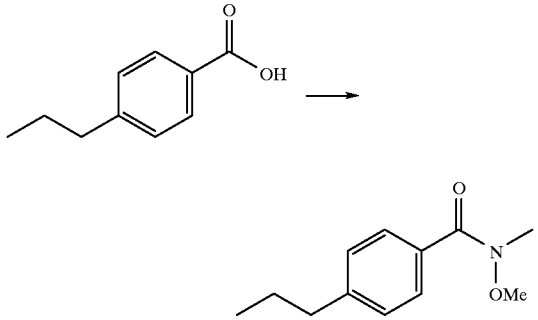

A mixture of 4-n-propylbenzoic acid (10.0 g), 1-hydroxybenzotriazole hydrate (8.20 g), 1-(3-N,N-dimethylaminopropyl)-3-ethylcarbodiimide hydrochloride (21.5 g) and dichloromethane (1000 ml) was treated dropwise with triethylamine (42.6 ml) and N,O-dimethylhydroxylamine hydrochloride (6.6 g). The mixture was stirred overnight at room temperature and then treated with water (700 ml). The organic layer was separated, washed with 2N aqueous hydrochloric acid (4×500 ml) and then saturated aqueous sodium bicarbonate solution (4×500ml). The organic phase was dried (MgSO$_4$) and concentrated to give the title compound as a clear oil (10.8 g). $^1$H-NMR (CDCl$_3$): δ=0.95(t,3H), 1.65(m,2H), 2.60(t, 2H), 3.36(s,3H), 3.58(s,3H), 7.20(d,2H), 7.60(d, 2H) ppm.

PREPARATION 8

1,1-Dimethoxy-1-(4-ethylphenyl)pentane

This compound was prepared by the method outlined in Preparation 5 from 1-(4-ethylphenyl)pentan-1-one which, in turn, was prepared by methods similar to those outlined in Preparations 6 and 7.

We claim:

1. A compound of formula (I):

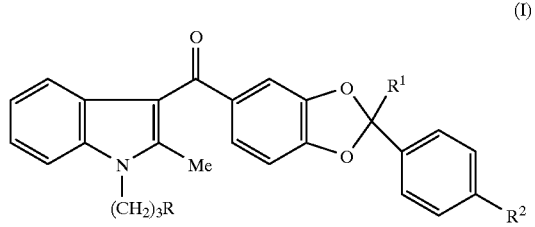

and the pharmaceutically acceptable base salts thereof, wherein: R is CO$_2$R$^{12}$ where R$^{12}$ is H or a C$_1$–C$_6$ alkyl ester, and either (a) R$^1$ is

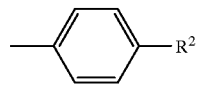

and R$^2$ is F, Cl, Br, I, CH$_3$ or CF$_3$, or (b) R$^1$ is C$_3$–C$_6$ alkyl and R$^2$ is C$_2$–C$_4$ alkyl.

2. A compound according to claim 1, in which R is CO$_2$H.

3. A compound according to claim 1, in which R$^1$ is C$_3$–C$_4$ alkyl.

4. A compound according to claim 3, in which R$^1$ is n-butyl.

5. A compound according to claim 3 in which R$^2$ is ethyl or n-propyl.

6. A compound according to claim 1 in which, R$^1$ is

and R$^2$ is F, Cl, Br or I.

7. A compound selected from:
   4-[3-([2,2-p-chlorophenyl-1,3-benzodioxolan-5-yl] carbonyl)-2-methylindol-1-yl]butanoic acid;
   4-[3-([2-butyl-(4-n-propylphenyl)-1,3-benzodioxolan-5-yl]carbonyl)2-methylindol-1-yl]butanoic acid;
   4-[3-([2-butyl-2-(4-ethylphenyl)-1,3-benzodioxolan-5-yl]carbonyl)2-methylindol-1-yl]butanoic acid;
   ethyl-4-[3-([2,2-p-chlorophenyl-1,3-benzodioxolan-5-yl) carbonyl)2-methylindol-1-yl]butanoate;
   ethyl-4-[3-([2-butyl-2-{4-n-propylphenyl)-1,3-benzodioxolan-5-yl]carbonyl)2-methylindol-1-yl] butanoate; and
   ethyl-4-[3-([2-butyl-2-(4-ethylphenyl)-1,3-benzodioxolan-5-yl]carbonyl)2-methylindol-1-yl] butanoate,
and pharmaceutically acceptable base salts thereof.

8. A compound according to claim 1, wherein said salt is a sodium, potassium, N-benzyl-N-(2-phenylethyl)amine or 1-adamantylamine salt.

9. A compound according to claim 1, wherein said compound is 4-[3-([2,2-bis (p-chlorophenyl)-1,3-benzodioxolan-5-yl]carbonyl)-2-methylindol-[2]1-yl] butanoic acid;
   4-[3-([2-butyl-2-(4-n-propylphenyl)-1,3-benzodioxolan-5-yl]carbonyl)-2-methylindol-1-yl]butanoic acid;
   4-[3-([2-butyl-2-(4-ethylphenyl)-1,3-benzodioxolan-5-yl]carbonyl)-2-methylindol-1-yl]butanoic acid;
   ethyl 4-[3-([2,2-bis p-chlorophenyl)-1,3-benzodioxolan-5-yl]carbonyl)-2-methylindol-1-yl]butanoate;
   ethyl 4-[3-([2[,]-butyl-2-(4-n-propylphenyl)-1,3-benzodioxolan-5-yl]carbonyl)-2-methylindol-1-yl] butanoate;
   ethyl 4-[3-([2[,]-butyl-2-(4-ethylphenyl)-1,3-benzodioxolan-5-yl]carbonyl)-2-methylindol-1-yl] butanoateg
and the pharmaceutically acceptable salts thereof.

* * * * *